| United States Patent [19] | [11] | 4,395,542 |
|---|---|---|
| Sury | [45] | Jul. 26, 1983 |

[54] PROCESS FOR REMOVING TRACE AMOUNTS OF EPICHLOROHYDRIN FROM HEAT SENSITIVE GLYCIDYL PRODUCTS

[75] Inventor: Yel S. Sury, Warwick, R.I.

[73] Assignee: Ciba-Geigy Corporation, Ardsley, N.Y.

[21] Appl. No.: 340,674

[22] Filed: Jan. 19, 1982

[51] Int. Cl.³ .................. C08G 59/00; C08G 59/02
[52] U.S. Cl. ............................ 528/481; 528/87; 528/483; 528/501; 528/502; 549/514; 549/517
[58] Field of Search ............... 528/87, 481, 483, 501, 528/502; 549/514, 517

[56] References Cited

U.S. PATENT DOCUMENTS 2,824,855  2/1958  Freeman et al. ............... 528/501
3,720,645  3/1973  Nistri et al. .................... 528/87

FOREIGN PATENT DOCUMENTS 5056104  10/1978  Japan ........................... 528/501

OTHER PUBLICATIONS

I. P. Andreev et al., Chem. Abst. 81, 122835u (1974).

*Primary Examiner*—Lester L. Lee
*Attorney, Agent, or Firm*—Luther A. R. Hall

[57] ABSTRACT

Epichlorohydrin levels in heat sensitive glycidyl products are reduced from a few thousand ppm, an unacceptable level, to only a few ppm or to a non-detectable level by use of a multistage stripping column with or without inert gas purging without decomposition of the heat sensitive glycidyl products. Such glycidyl products are useful in epoxy resins particularly as crosslinking agents.

10 Claims, No Drawings

PROCESS FOR REMOVING TRACE AMOUNTS OF EPICHLOROHYDRIN FROM HEAT SENSITIVE GLYCIDYL PRODUCTS

FIELD OF THE PRESENT INVENTION

The present invention pertains to a process of reducing the level of residual epichlorohydrin in heat sensitive glycidyl products to very low and acceptable levels of from zero to a few ppm by use of a multistage stripping column with or without inert gas purging.

BACKGROUND OF THE INVENTION

Epichlorohydrin is a key ingredient in the preparation of glycidyl products and epoxy resins. Epichlorohydrin is also suspected of being a carcinogen. Accordingly, it is imperative for considerations of health, safety and economic prudence that the epichlorohydrin content of epoxy resin and glycidyl products be reduced to the lowest feasible levels to minimize any hazards involved with residual epichlorohydrin.

Conventional methods to strip epichlorohydrin from epoxy resin or glycidyl products include steam stripping, inert gas purging or falling film evaporation. However, none of these methods is satisfactory for thermally or hydrolytically unstable materials. Steam stripping clearly cannot be used with products which are not stable at high temperature in the presence of water. Gas purging or falling film evaporation can only reduce the epichlorohydrin level in thermally unstable products to a level of a few hundred ppm, still far too high for acceptability.

OBJECTS OF THE INVENTION

The object of the instant invention is a method or process to prepare an epoxy resin or product containing glycidyl groups which is essentially free of residual epichlorohydrin and associated volatile materials which involves heating the epoxy resin or product containing glycidyl groups to a temperature at which said resin or product flows easily, but at which temperature the resin or product is still thermally stable and then subjecting said heated resin or product to multistage stripping under vacuum.

A further object of the invention is to the method which involves the concomitant purging of the heated resin or product with an inert gas during the multistage stripping step.

DETAILED DISCLOSURE

The instant invention is a method of preparing an epoxy resin or product containing glycidyl groups, essentially free of residual epichlorohydrin and associated volatile materials, which comprises heating an epoxy resin or product containing glycidyl groups, which still contains excessive amounts of epichlorohydrin and associated volatile material, typically 1000 ppm or more, to a temperature of 60° to 250° C., preferably 80° to 180° C., a temperature sufficient to allow said resin or said product to flow easily, but insufficient to cause thermal decomposition thereof, and subjecting the heated resin or product to multistage stripping in a packed column or multistage evaporation stripper at a temperature of 60° to 250° C., preferably 80° to 180° C., and at a pressure of 1 to 500 mm Hg, preferably 6 mm Hg or less, to reduce the level of epichlorohydrin and associated volatile material in the stripped resin or product to less then 100 ppm, preferably less than 10 ppm.

The instant method can be carried out without the use of concomitant purging with an inert gas, preferably nitrogen, during the multistage stripping step. Nonetheless it is often beneficial to employ such inert gas purging during the multistage stripping step in order to facilitate the removal of the residual epichlorohydrin and associated volatile material to acceptably low levels. Indeed, when inert gas purging is used, the temperature required for optimum results in the instant process may be as much as 30° lower than when no inert gas purging is used in order to obtain the same results, i.e., the same low level of epichlorohydrin content in the stripped resin or product.

Although the instant method is applicable to any epoxy resin or product containing glycidyl groups, which resin or product contains free epichlorohydrin or related volatile materials therein, it is particularly useful in preparing epoxy resins or products containing glycidyl groups which are thermally or hydrolytically unstable.

Thus while epoxy resins such as 2,2-bis(4-glycidyloxy-phenyl)propane, ARALDITE 6010, which is thermally and hydrolytically stable may be used advantageously in the instant method, the instant process is particularly advantageous for use with products which are thermally and/or hydrolytically less stable such as N,N,O-triglycidyl-p-aminophenol, N,N,N',N'-tetraglycidyl-4,4'-methylenedianiline, triglycidyl isocyanurate, and N,N-diglycidyl-5,5-dialkylhydantoins such as the diglycidyl derivatives of dimethylhydantoin, methylethylhydantoin, ethylamylhydantoin and pentamethylenehydantoin.

The instant method may be applied to epoxy resins or products containing glycidyl groups which resin or product contains any amount of free epichlorohydrin from adventitious quantities to quantities in excess of 1000 ppm of epichlorohydrin. The instant process provides an expeditious method of reducing epichlorohydrin levels in excess of 1000 ppm to levels well below 100 ppm and often to essentially zero or a non-detectable level.

The temperature at which the stripping operation takes place is dictated by the stability of the epoxy resin or product containing glycidyl groups, the tenacity with which the epichlorohydrin adheres to said resin or product and practical considerations of time, energy and the like dictated by economics. There are clearly tradeoffs of temperature versus time; rate of flow of resin or product through the stripper (residence time); relative flow rate of nitrogen or other inert purging gas; and reduced pressure (vacuum). Depending on the epoxy resin or product containing glycidyl groups which is to be stripped of epichlorohydrin, it is contemplated that one would use the minimum temperature to assure minimum thermal decomposition of said resin or product at such minimum nitrogen flow rate, if any inert purging gas is even to be used at all, and at a reduced pressure consistent with facile operation of the equipment being used to allow the maximum flow rate of the resin or product through the stripper still yielding a stripped resin or product meeting acceptable epichlorohydrin levels for the stripped resin or product.

The specific type of multistage stripper is not critical. It is contemplated that any packed column or vacuum stripper providing multistage stripping capabilities can be used in the instant process.

A convenient stripper is the Continuous Vacuum Stripper manufactured by Artisan Industries having 26 theoretical plates which was used in the Examples 5-8. The instant process is not limited to this specific stripper as is seen in Examples 1-4 where a relatively rudimentary packed column stripper was used satisfactorily.

The following examples are presented for the purpose of illustration only and are not to be construed to limit the nature or scope of the instant invention in any manner whatsoever.

EXAMPLES 1-4

A vertical jacketed column of 0.5 inch (1.27 cm) diameter was packed to a height of 18 inches (45.72 cm) with fine wire mesh. The column was fitted with a jacket through which temperature controlled polyethylene glycol was circulated to maintain the desired temperature in the column. The column was fitted with a source of vacuum with vacuum gauge and an inlet at the bottom of the column for introducing heated nitrogen as a purging gas. The nitrogen was heated to the temperature of the column by an external heat source, and the rate of flow of nitrogen gas was monitored and controlled by a flowmeter and control valve.

An epoxy resin or product containing glycidyl groups having over 2000 ppm of epichlorohydrin present therein, was placed in a 1000 ml bottom-outlet flask fitted with a thermowatch control mantle attached to the top of the packed column.

The flask and contents were then heated to a temperature sufficient to allow the epoxy resin or product containing glycidyl groups to flow readily, but to a temperature insufficient to cause the thermal decomposition thereof. This temperature was the same as that maintained in the packed column and of the heated nitrogen purging gas. Heated nitrogen purging gas was admitted to the column and a pressure (vacuum) of 410 mm Hg was imposed on the system. The heated epoxy resin or product containing glycidyl groups was allowed to flow into the packed column by gravity feed.

The stripped resin or product was collected at the bottom of the packed column with the flow rate determined by timing the run and weighing the resin or product. The flow rate was adjusted to the desired level by use of a metering valve on the bottom-outlet flask.

The stripped resin or product containing glycidyl groups was analyzed for epichlorohydrin content to measure the effectiveness of the stripping step. After the analysis was completed, the stripped resin or product containing glycidyl groups was passed through the packed column again for as many times as was needed to reduce the level of epichlorohydrin to less than 10 ppm.

On Table 1 are listed the results of these stripping experiments using four different starting materials showing the number of passes through the column required to reduce the epichlorohydrin levels to less than 10 ppm.

TABLE 1

| | Epichlorohydrin Concentration (ppm) vs. Number of Passes Through Column | | | |
|---|---|---|---|---|
| Example | 1 | 2 | 3 | 4 |
| Resin or Product* | A | B | C | D |
| Temperature °C. | 130 | | 120 | 120 | 120 |
| Ratio (g/g) N$_2$/Resin (Product) | 0.10 0.10 | 0.10 0.30 | 0.15 0.10 | 0.10 0.1 |
| Resin Rate g/minute | 10.4 4.9 | 8.9 3.2 | 8.1 10.2 | 11.3 6.3 |
| Passes Through Column | | | | |
| 0 | 201 3990 | 5176 3111 | 2882 3870 | 3500 2269 |
| 1 | 45 1747 | 1637 159 | 1548 3000 | 1840 1025 |
| 2 | 16 552 | 529 7 | 747 2591 | 1270 502 |
| 3 | 5 156 | 173 5 | 410 1140 | 940 325 |
| 4 | 0 44 | 95 0 | 262 680 | 515 250 |
| 5 | 35 | | 104 443 | 522 63 |
| 6 | 23 | | 53 470 | 381 79 |
| 7 | 4 | | 31 276 | 285 50 |
| 8 | 0 | | 18 180 | 240 40 |
| 9 | | | 13 | 167 21 |
| 10 | | | 9 | 93 31 |
| 11 | | | 9 | 90 |
| 12 | | | | 58 |
| 13 | | | | 42 |
| 14 | | | | 30 |
| 15 | | | | 17 |
| 16 | | | | 5 |

*A is 2,2-bis(4-glycidyloxyphenyl)propane, ARALDITE 6010.
B is N,N—diglycidyl-5,5-pentamethylenehydantoin.
C is N,N,O—triglycidyl-p-aminophenol.
D is N,N,N',N'—tetraglycidyl-4,4'-methylenedianiline.

The number of passes through the packed column to reduce the epichlorohydrin content to an acceptable level varied depending on the nature of the resin or product containing glycidyl groups.

It is clear that many passes through a short column are essentially equivalent to fewer passes through a longer column. Likewise, the imposition of lower operating pressure (higher vacuum) would facilitate the reduction in residual epichlorohydrin levels.

The operating flow rate ratios of nitrogen/resin (or product) were controlled to the indicated levels to prevent flooding of the column. Residence time of the resin or product in the column was between 60 and 90 seconds per pass depending on flow rate.

EXAMPLES 5-8

Using the same general procedure of Examples 1-4, four materials, having between 447 and 20,050 ppm of epichlorohydrin present therein, were subjected to multistage stripping by a single pass through a large Continuous Vacuum Stripper manufactured by Artisan Industries. This stripper was 2 inches (5.08 cm) in diameter and had 26 theoretical plates.

The stripper was operated at a maximum pressure of 6 mm Hg and the residence time of the material being stripped in the stripper was less than 1 minute.

The result of the multistage stripping are given in Tables 2-5.

TABLE 2

Stripping of 2,2-bis(4-glycidyloxyphenyl)propane ARALDITE 6010

| | | | | Content of Epichlorohydrin ppm | |
|---|---|---|---|---|---|
| Example 5 | Temperature °C. | Resin Rate Kg/hour | N$_2$/Resin weight ratio | Original Resin | Stripped Resin |
| a | 122 | 41.58 | 0 | 3100 | 116 |
| b | 124 | 41.36 | 0.053 | 3000 | 96 |

TABLE 2-continued

Stripping of 2,2-bis(4-glycidyloxyphenyl)propane ARALDITE 6010

| Example 5 | Temperature °C. | Resin Rate Kg/hour | N₂/Resin weight ratio | Content of Epichlorohydrin ppm | |
|---|---|---|---|---|---|
| | | | | Original Resin | Stripped Resin |
| c | 124 | 42.24 | 0.158 | 2900 | 22 |
| d | 122 | 23.54 | 0.273 | 2200 | 1 |
| e | 137 | 35.42 | 0 | 2800 | 18 |
| f | 137 | 35.64 | 0.0625 | 2600 | 13 |
| g | 134 | 46.20 | 0.143 | 2100 | 9 |
| h | 136 | 25.96 | 0.25 | 1800 | none* |
| i | 149 | 51.48 | 0 | 1800 | 9 |
| j | 150 | 52.36 | 0.042 | 1800 | none* |
| k | 151 | 51.70 | 0.125 | 1800 | none* |

*No epichlorohydrin could be detected in the stripped resin.

TABLE 3

Stripping of N,N,O—Triglycidyl-p-aminophenol

| Example 6 | Temperature °C. | Product Rate Kg/hour | N₂/Product weight ratio | Content of Epichlorohydrin ppm | |
|---|---|---|---|---|---|
| | | | | Original Product | Stripped Product |
| a | 107 | 26.18 | 0.25 | 3300 | 54 |
| b | 105 | 11.66 | 0.6 | 3300 | 37 |
| c | 106 | 9.02 | 0.75 | 3300 | 14 |
| d | 106 | 11.66 | 1.0 | 3300 | 10 |
| e | 121 | 51.26 | 0 | 3500 | 78 |
| f | 122 | 50.60 | 0.13 | 3500 | 25 |
| g | 121 | 34.32 | 0.19 | 3500 | 13 |
| h | 122 | 20.24 | 0.33 | 3400 | 7 |
| i | 121 | 10.12 | 0.65 | 3400 | none* |
| j | 134 | 49.94 | 0 | 3300 | 29 |
| k | 136 | 49.06 | 0.045 | 3300 | 20 |
| l | 135 | 49.06 | 0.14 | 3300 | 7 |
| m | 135 | 35.86 | 0.19 | 3300 | 8 |
| n | 134 | 22.88 | 0.29 | 3300 | 1 |
| o | 151 | 50.38 | 0 | 3300 | 4 |
| p | 151 | 47.30 | 0 | 3300 | 4 |
| q | 150 | 48.84 | 0.045 | 3300 | 2 |
| r | 151 | 45.54 | 0.048 | 3300 | 4 |
| s | 149 | 47.30 | 0.136 | 3300 | none* |

*No epichlorohydrin could be detected in the stripped product.

TABLE 4

Stripping of N,N,N',N'—Tetraglycidyl-4,4'-methylenedianiline

| Example 7 | Temperature °C. | Product Rate Kg/hour | N₂/Product weight ratio | Content of Epichlorohydrin ppm | |
|---|---|---|---|---|---|
| | | | | Original Product | Stripped Product |
| a | 121 | 62.04 | 0 | 2900 | 730 |
| b | 122 | 52.14 | 0.125 | 2800 | 830 |
| c | 121 | 41.36 | 0.158 | 2700 | 870 |
| d | 122 | 35.64 | 0.188 | 2700 | 490 |
| e | 122 | 22.22 | 0.33 | 2600 | 340 |
| f | 121 | 12.10 | 0.545 | 2500 | 380 |
| g | 135 | 46.42 | 0 | 2400 | 410 |
| h | 135 | 48.62 | 0.136 | 2400 | 500 |
| i | 135 | 36.08 | 0.188 | 2400 | 390 |
| j | 135 | 11.66 | 0.6 | 2400 | 130 |
| k | 150 | 49.06 | 0 | 2400 | 220 |
| l | 150 | 47.08 | 0.048 | 2400 | 240 |
| m | 149 | 48.18 | 0.136 | 2300 | 210 |
| n | 150 | 17.82 | 0.375 | 2200 | 130 |
| o | 162 | 54.12 | 0 | 2200 | 110 |
| p | 160 | 47.96 | 0.045 | 2100 | 110 |

TABLE 5

Stripping of Triglycidyl Isocyanurate

| Example 8 | Temperature °C. | Product Rate Kg/hour | N₂/Product weight ratio | Content of Epichlorohydrin ppm | |
|---|---|---|---|---|---|
| | | | | Original Product | Stripped Product |
| a | 126 | 12.54 | 0 | 447 | 111 |
| b | 126 | 16.94 | 0.011 | 447 | 183 |
| c | 133 | 47.08 | 0.008 | 447 | 92 |
| d | 122 | 7.04 | 0 | 447 | 95 |
| e | 160 | 61.60 | 0 | 447 | 23 |
| f | 143 | 19.14 | 0 | 447 | 12 |
| g | 159 | 17.82 | 0.144 | 447 | 7 |
| h | 152 | 15.62 | 0.220 | 447 | 4 |
| i | 166 | 110.44 | 0 | 20,050 | 459 |
| j | 167 | 88.44 | 0 | 20,050 | 152 |
| k | 164 | 17.16 | 0 | 20,050 | 12 |
| l | 143 | 13.20 | 0.130 | 20,050 | 8 |
| m | 142 | 11.16 | 0.294 | 20,050 | 15 |
| n | 157 | 82.50 | 0.042 | 20,050 | 89 |
| o | 161 | 95.04 | 0.045 | 20,050 | 55 |

Epichlorohydrin was stripped from 2,2-bis(4-glycidyloxyphenyl)propane readily as seen in Examples 5 d, g and i (Table 2). The epichlorohydrin level was reduced from 2200 ppm to less than 10 ppm at a temperature of 122° C. with the nitrogen/resin weight ratio of 0.273; from 2100 ppm to less than 10 ppm at 134° C. with a N₂/resin ratio of 0.143; and from 1800 ppm to less than 10 ppm at 149° C. without inert gas purging.

Epichlorohydrin was also successfully stripped from N,N,O-triglycidyl-p-aminophenol as seen in Examples 6 d, h, o and p (Table 3). The epichlorohydrin level was reduced from 3300 ppm to less than 10 ppm at a temperature of 106° C. with the nitrogen/product weight ratio of 1.0; from 3400 ppm to less than 10 ppm at 122° C. with the N₂/product ratio of 0.33; and from 3300 ppm to less than 10 ppm at 151° C. without inert gas purging.

With N,N,N',N'-tetraglycidyl-4,4'-methylenedianiline, stripping of the residual epichlorohydrin was more difficult. As is seen in Examples 7 n and o (Table 4), the epichlorohydrin level was reduced from 2200 ppm to 130 ppm at 150° C. with the nitrogen/product weight ratio of 0.375; and from 2200 ppm to 110 ppm at 162° C. without inert gas purging. The data on Table 1 show that it should be possible to reduce residual epichlorohydrin to below 10 ppm by employing higher temperatures, more plates, a higher nitrogen ratio, or some combination of these.

With triglycidyl isocyanurate, stripping of the residual epichlorohydrin was readily carried out as seen in Examples 8 g, l, f and k (Table 5). The epichlorohydrin level was reduced from 447 ppm to less than 10 ppm at a temperature of 159° C. and a nitrogen/product weigh ratio of 0.144; from 20,050 ppm (2%) to less than 10 ppm at 143° C. and a N₂/product ratio of 0.130; from 447 ppm to 12 ppm at 143° without inert gas purging; and from 20,050 ppm to 12 ppm at 164° C. without inert gas purging.

Analysis of the stripped products of Examples 6 p and 7 o indicated these heat sensitive products were in all essential aspects unchanged compared to the original product except for viscosity and hydrolyzable chlorine values. Since the epoxy value and gas phase chromatography (GPC) were essentially the same, the differences in viscosity (up) and hydrolyzable chlorine (down) must be attributed to the reduction in epichlorohydrin content of the product before and after stripping. These data are given in Table 6.

TABLE 6

| Property | Product of Example 6 Before Stripping | Product of Example 6 After Stripping | Product of Example 7 Before Stripping | Product of Example 7 After Stripping |
| --- | --- | --- | --- | --- |
| Visual Appearance | dark amber clear | dark amber clear | dark brown clear | dark brown clear |
| Epoxy Value eq/100g | 0.90 | 0.09 | 0.79 | 0.75 |
| hydrolyzable chlorine % | 0.27 | 0.16 | 0.18 | 0.13 |
| Ionic chloride ppm | — | — | 0.69 | 0.76 |
| Volatiles % | 1.23 | 0.09 | 0.01 | 0.11 |
| Water % | 0.25 | 0.30 | — | — |
| Viscosity cp at 25°C. | 2760 | 3700 | 28,400 | 29,600 |
| GPC High MW material | 8.6 | 8.5 | 13.8 | |
| Dimer | 16.7 | 17.0 | 18.4 | 18.4 |
| Unkown | 4.3 | 4.1 | 5.9 | 5.9 |
| monomer | 70.4 | 70.4 | 61.4 | 60.8 |

In like manner analysis of the stripped products of Examples 8 h and 8 i indicated that the stripping operation did not affect the quality of the stripped product. The properties of the original triglycidyl isocyanurate and the stripped products were essentially the same except for volatiles (%) with the stripped product having much lower volatiles as would be consistent with the removal of the residual epichlorohydrin. These analytical data are given on Table 7.

TABLE 7

| Property | Product of Example 8h Before Stripping | Product of Example 8h After Stripping | Product of Example 8i Before Stripping | Product of Example 8i After Stripping |
| --- | --- | --- | --- | --- |
| Visual Appearance | white solid crystalline | white solid crystalline | white solid crystalline | white solid crystalline |
| Epoxy value eq/100g | 0.900 | 0.897 | 0.913 | 0.894 |
| Hydrolyzable chlorine % | 0.54 | 0.46 | 0.60 | 0.52 |
| Volatiles % | 0.17 | 0.08 | 0.50 | 0.09 |
| Water % | 0.28 | 0.46 | 0.29 | 0.29 |
| Viscosity cps at 25° C. | 94 | 109 | — | 114 |

What is claimed is:

1. A method of preparing an epoxy resin or product containing glycidyl groups, essentially free of residual epichlorohydrin and associated volatile material, which comprises heating an epoxy resin or product containing glycidyl groups, which still contains excessive amounts of residual epichlorohydrin and associated volatile materials, to a temperature of 60° to 250° C., a temperature sufficient to allow said resin or said product to flow easily, but insufficient to cause thermal decomposition thereof, and passing the heated resin or product one or more times through a packed column or multistage evaporation stripper, to effect multistage stripping of said resin or product, at a temperature of 60° to 250° C. and at a pressure of 1 to 500 mm Hg, to reduce the level of epichlorohydrin and associated volatile materials in the heated resin or product to less than 10 ppm.

2. A method according to claim 1 wherein the epoxy resin or product containing glycidyl groups is heated to a temperature of 80° to 180° C. and is subjected to multistage stripping at a temperature of 80° to 180° C.

3. A method according to claim 1 wherein the multistage stripping is carried out at a pressure of 6 mm Hg or less.

4. A method according to claim 1 wherein the heated epoxy resin or product containing glycidyl groups is purged with an inert gas during the multistage stripping.

5. A method according to claim 4 wherein the inert gas is nitrogen.

6. A method according to claim 1 wherein the epoxy resin is 2,2-bis(4-glycidyloxyphenyl)propane.

7. A method according to claim 1 wherein the product containing glycidyl groups is N,N,O-triglycidyl-p-aminophenol.

8. A method according to claim 1 wherein the product containing glycidyl groups is N,N,N',N'-tetraglycidyl-4-4'-methylenedianiline.

9. A method according to claim 1 wherein the product containing glycidyl groups is triglycidyl isocyanurate.

10. A method according to claim 1 wherein the product containing glycidyl groups is N,N-diglycidyl-5,5-pentamethylenehydantoin.

* * * * *